(12) United States Patent
Belanger et al.

(10) Patent No.: US 8,936,617 B2
(45) Date of Patent: Jan. 20, 2015

(54) LOCKABLE ATTACHMENT AND STYPTIC DEVICE INCLUDING SAME

(75) Inventors: Guy Belanger, St-Bruno (CA); Ben Gendron, Beaconsfield (CA); Normand Mercier, Sant-Damien de Buckland (CA)

(73) Assignee: Benrikal Services Inc., St-Bruno (CA)

( * ) Notice: Subject to any disclaimer, the term of this patent is extended or adjusted under 35 U.S.C. 154(b) by 170 days.

(21) Appl. No.: 13/813,543

(22) PCT Filed: Aug. 9, 2011

(86) PCT No.: PCT/CA2011/000903
§ 371 (c)(1),
(2), (4) Date: Jan. 31, 2013

(87) PCT Pub. No.: WO2012/019281
PCT Pub. Date: Feb. 16, 2012

(65) Prior Publication Data
US 2013/0131721 A1    May 23, 2013

Related U.S. Application Data

(60) Provisional application No. 61/344,501, filed on Aug. 9, 2010.

(51) Int. Cl.
*A61B 17/08* (2006.01)
*A61B 17/00* (2006.01)
*A61B 17/12* (2006.01)
*A61B 17/132* (2006.01)
*A44B 19/24* (2006.01)

(52) U.S. Cl.
CPC ............ *A61B 17/0057* (2013.01); *A61B 17/12* (2013.01); *A61B 17/1325* (2013.01); *A44B 19/24* (2013.01); *A61B 2017/12004* (2013.01)
USPC ......................................................... 606/213

(58) Field of Classification Search
CPC . A61B 17/0057; A61B 17/1325; A61B 19/24
USPC ................................... 606/157, 201, 203, 213
See application file for complete search history.

(56) References Cited

U.S. PATENT DOCUMENTS

| | | |
|---|---|---|
| 134,052 A | 12/1872 | Gurley |
| 3,149,808 A | 9/1964 | Weckesser |
| 3,197,829 A | 8/1965 | Caveney et al. |
| 3,258,819 A | 7/1966 | Weckesser |
| 3,300,825 A | 1/1967 | Andreasen |
| 3,494,002 A | 2/1970 | Heinrich |
| 3,845,575 A | 11/1974 | Boden |
| 3,861,003 A | 1/1975 | Boden |
| 3,900,922 A | 8/1975 | McCormick |

(Continued)

*Primary Examiner* — Victor Nguyen

(57) ABSTRACT

A lockable flexible element including an attachment and a substantially elongated and flexible body defining a body first end and a substantially opposed body second end, the body defining a body serrated surface substantially longitudinally spaced apart from the body second end. The attachment includes a collar provided substantially adjacent the body second end; a tongue provided at least partially inside the collar and extending substantially longitudinally thereinto, the tongue defining a tongue serrated surface, the tongue being deformable between a tongue extended configuration and a tongue retracted configuration; and a safety catch removably insertable between the tongue and the collar with the tongue between the body serrated surface and the safety catch.

22 Claims, 6 Drawing Sheets

(56) References Cited

U.S. PATENT DOCUMENTS

| | | |
|---|---|---|
| 3,900,923 A | 8/1975 | Thomas |
| 3,909,884 A | 10/1975 | Weckesser |
| 4,008,512 A | 2/1977 | Prodel |
| 4,128,220 A | 12/1978 | McNeel |
| 4,182,338 A | 1/1980 | Stanulis |
| 4,314,568 A | 2/1982 | Loving |
| 4,479,495 A | 10/1984 | Isaacson |
| 4,653,155 A | 3/1987 | Hara |
| 4,676,535 A | 6/1987 | Mautner |
| 4,727,630 A | 3/1988 | Alan |
| 5,084,062 A | 1/1992 | Sturm |
| 5,184,352 A | 2/1993 | Maufette |
| 5,269,803 A | 12/1993 | Geary et al. |
| 5,304,188 A | 4/1994 | Marogil |
| 5,367,749 A | 11/1994 | Takeuchi |
| 5,414,904 A | 5/1995 | Sampson |
| 5,451,234 A | 9/1995 | Wassermann |
| 5,512,056 A | 4/1996 | Stevens et al. |
| 5,514,155 A * | 5/1996 | Daneshvar .................. 606/201 |
| 5,535,485 A | 7/1996 | Kirchner |
| 5,695,520 A | 12/1997 | Bruckner et al. |
| 5,729,871 A | 3/1998 | Schulte |
| 5,873,890 A | 2/1999 | Porat |
| 5,890,265 A | 4/1999 | Christian et al. |
| 5,893,870 A | 4/1999 | Talen et al. |
| 5,901,416 A | 5/1999 | Mears |
| 6,217,601 B1 | 4/2001 | Chao |
| 6,230,369 B1 | 5/2001 | Steadman |
| 6,986,779 B2 | 1/2006 | Begley et al. |
| 7,281,302 B2 | 10/2007 | Hewes |
| 7,329,270 B2 * | 2/2008 | Åkerfeldt et al. ............. 606/201 |
| 7,842,067 B2 | 11/2010 | Esposito |
| 7,900,324 B2 | 3/2011 | Ginocchio |
| 2003/0229375 A1 | 12/2003 | Fleischer |
| 2003/0229972 A1 | 12/2003 | Welsh |
| 2005/0062608 A1 | 3/2005 | Costa |
| 2005/0125025 A1 | 6/2005 | Rioux |
| 2006/0162130 A1 | 7/2006 | Cook |
| 2006/0190026 A1 | 8/2006 | Sanders |
| 2007/0088386 A1 | 4/2007 | Babaev |
| 2008/0262534 A1 | 10/2008 | O'Neil |
| 2008/0287975 A1 | 11/2008 | Weaner et al. |
| 2009/0281565 A1 | 11/2009 | McNeese |
| 2010/0125979 A1 | 5/2010 | Hienekamp |
| 2011/0072623 A1 | 3/2011 | Vermeer et al. |
| 2011/0295310 A1 | 12/2011 | Bao et al. |

\* cited by examiner

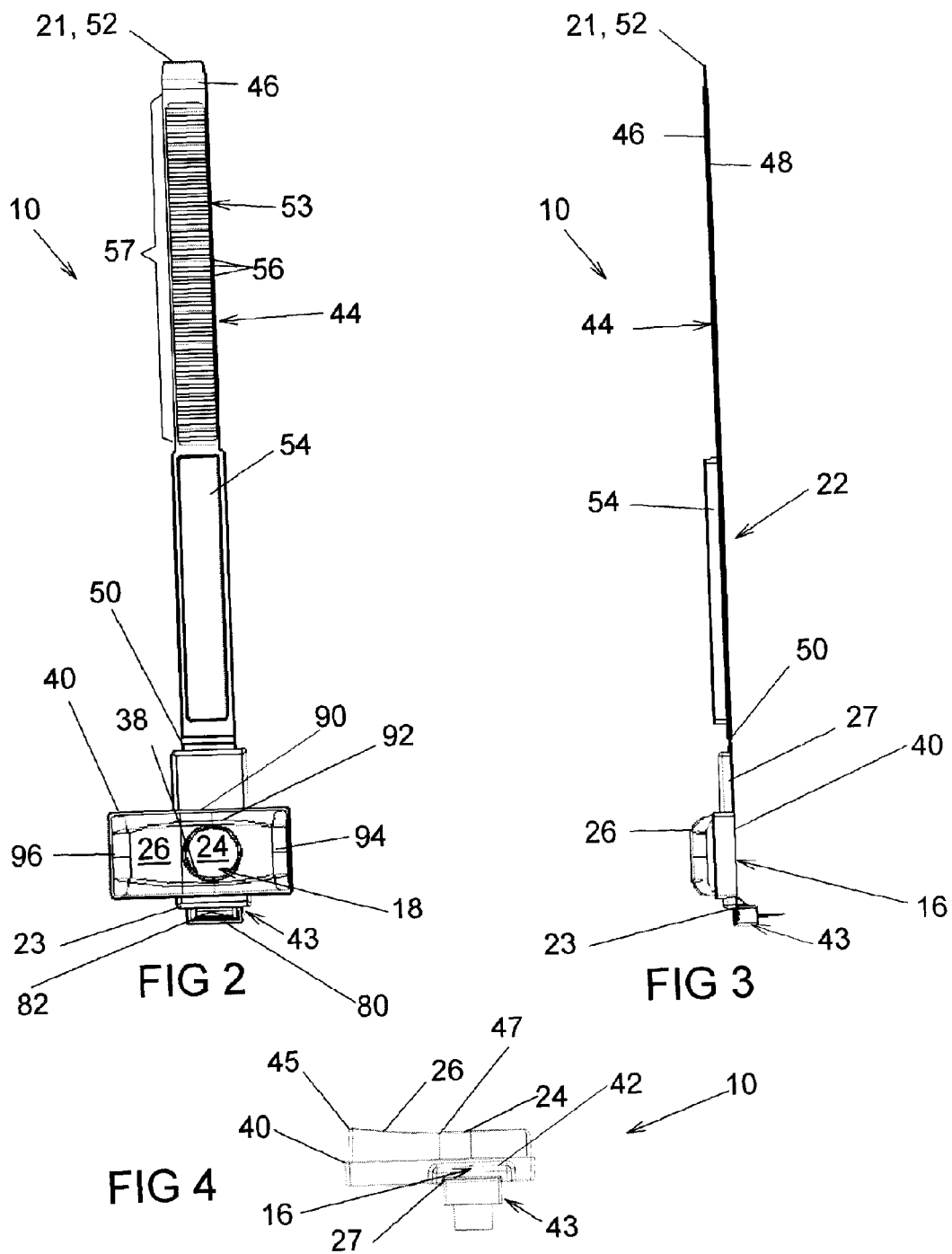

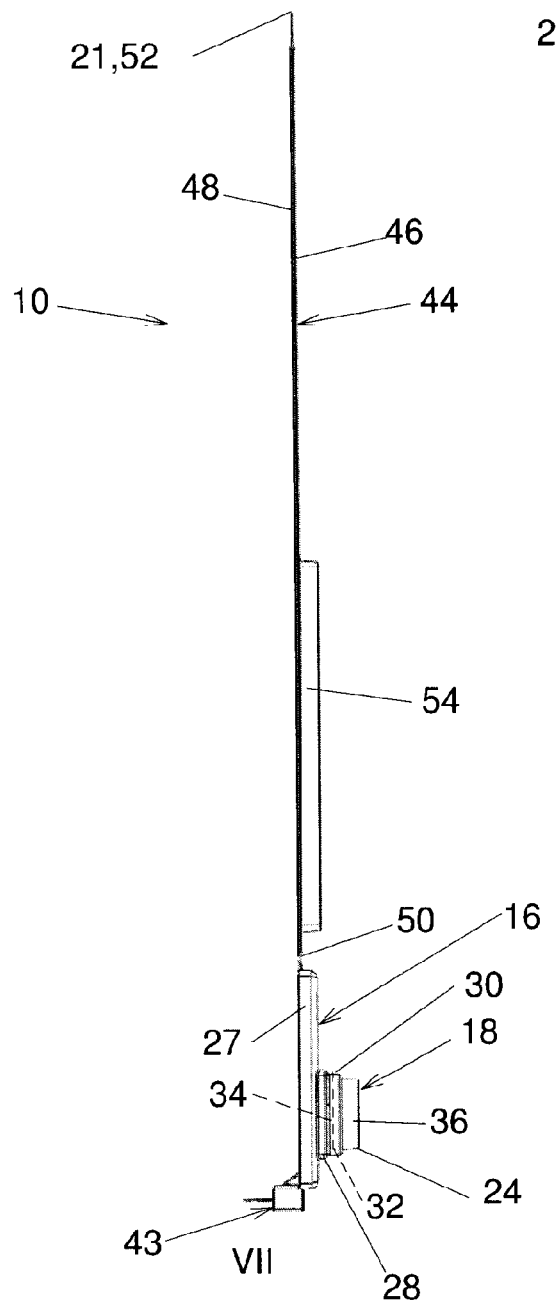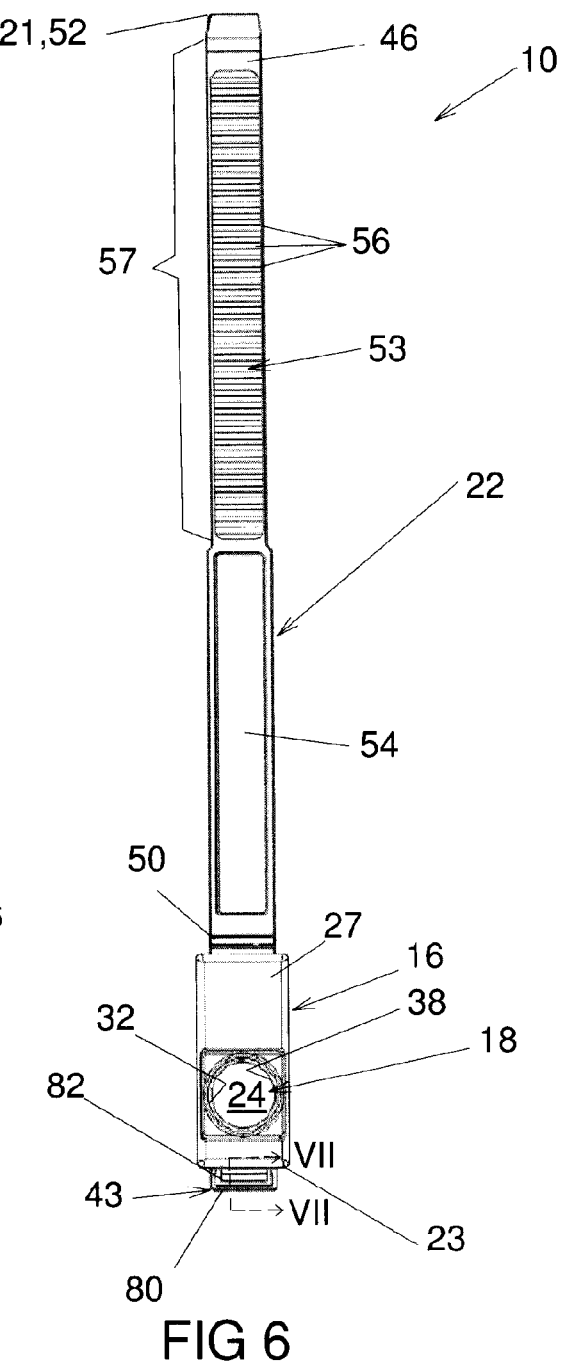

LOCKABLE ATTACHMENT AND STYPTIC DEVICE INCLUDING SAME

FIELD OF THE INVENTION

The present invention relates to the general field of attachments, usable for example for attaching two ends of an elongated flexible element to each other, and is particularly concerned with a lockable attachment. The present invention also relates to medical devices and is particularly concerned with a styptic device for hemostatically sealing percutaneous vascular punctures that incorporates such an attachment.

BACKGROUND

There exists a plurality of medical and/or surgical procedures that are carried out intravascularly or intralumenally. For example, in the treatment of vascular diseases, such as atherosclerosis, percutaneous angioplasty and stenting are now widely accepted procedures.

Such procedures usually involve the percutaneous puncture and insertion of a hollow needle through a patient's skin and muscle tissue into the vascular system. A guide wire is then typically passed through the needle lumen into the patient's blood vessel accessed by the needle. The needle may be removed, and an introducer sheath may be advanced over the guide wire into the vessel, for example, in conjunction with or subsequent to, a dilator.

A catheter or other device may then be advanced through a lumen of the introducer sheath and over the guide wire into position for performing a medical procedure such as, dilating the vessel, stenting of the latter, or the like.

In percutaneous transluminal coronary angioplasty, the catheter is typically introduced either in the radial or femoral artery and advanced through the artery to the coronary region. Catheters typically have a diameter in the range of one millimeter and four millimeters, hence creating a significant puncture in the artery. Also, during the procedure, the catheter may be twisted or otherwise manipulated as it is advanced to the treatment site, hence potentially causing a further enlargement of the puncture.

Upon completion of the procedure, the devices and introducer sheath may be removed, leaving a puncture site in the vessel wall. Such procedures hence unavoidably present the problem of stopping the bleeding at the percutaneous puncture site after the procedure has been completed and after the instrument and any introducer sheaths used therewith have been removed.

At present, such bleeding is sometimes stopped by the application of direct digital pressure over the puncture site by a trained physician or other suitably trained medical personnel. Such direct pressure has to be properly applied for a sufficiently long period of time for haemostasis to occur so that the opening is effectively closed against further bleeding. The application of direct digital pressure over the puncture site, although somewhat useful, nevertheless suffers from numerous drawbacks.

First, the direct digital pressure application procedure constitutes an inefficient, if not wasteful, use of medical professional services. For example, in the case of punctures into relatively high pressure vessels, such as into the femoral artery or superficial femoral arteries, the pressure may have to be applied for as long as forty-five minutes for haemostasis to occur.

Second, the application of digital pressure over a relatively long period of time may result in fatigue, numbness, stiffness and/or pain occurring in the fingers, hands, wrists and/or forearms of the practitioner performing the procedure. Furthermore, repetition of the procedure over a period of time may cause repetitive-type stress injuries, such as carpal tunnel syndrome or the like.

Still furthermore, although the procedure is typically performed with gloves there exists a possibility that the glove could already have, or may develop, a tear, thereby allowing direct pressurized digital contact with potentially contaminating bodily fluids.

Third, it is often difficult for an individual to exert digital pressure of optimal magnitude, especially over a relatively long period of time. The magnitude of the pressure exerted may however prove to be particularly important in some situations. Indeed, should the magnitude of the pressure be suboptimal, a bruise or haematoma may form at the entry site since internal bleeding of the punctured artery continues until clotting blocks the puncture. On the contrary, should the applied pressure be too great, this may result in a substantial reduction, if not virtual arrest, of the flow of blood through the vessel. This, in turn, may lead to thrombosis of the vessel with potentially serious complications.

Yet another drawback associated with the conventional digital application of pressure at the puncture site results from the fact that the instrument and any introducer sheath used therewith is typically completely withdrawn prior to the application of pressure at the puncture site. This results in a brief, yet vigorous, free-flow of blood through the puncture site, which may obscure the exact location of the puncture momentarily leading to further blood loss.

Still furthermore, the conventional method of digital pressure application of the puncture site is sometimes considered uncomfortable for the patient and requires that the patient remain immobilized in the operating room, catheter lab, holding area or the like, hence using up valuable space.

Some styptic devices as been shown in the prior art. However, such prior art devices suffer from numerous drawbacks. Indeed, prior art device generally suffer from being unergonomical to the user and uncomfortable to the patient. Prior art devices also suffer from being overall too complex, and, hence, relatively expensive and potentially unreliable.

Also, some of these devices take the form of bracelets that are tightened around a limb on which the puncture site is found. Many of these bracelets are secured in a loop using a serrated surface provided at one end of the bracelet engaging a serrated tongue provided at the other end of the bracelet, in a manner similar to the attachment of tie-wraps. Deforming the tongue allows release of the bracelet and its removal. There is in some of these prior art styptic device a risk that the tongue is inadvertently released, which could cause bleeding and other complications.

Accordingly, there exists a need for an improved styptic device for hemostatically sealing percutaneous vascular punctures and for improved attachments for elongated flexible elements. It is a general objective of the present invention to provide such an improved styptic device. It is also a general objective of the present invention to provide an improved tie-wrap-type attachment.

SUMMARY OF THE INVENTION

In a broad aspect, the invention provides a styptic device for substantially hemostatically sealing a percutaneous puncture in a blood vessel of a patient, the styptic device comprising: a bracelet defining a bracelet first end and a substantially opposed bracelet second end; and a compression element mechanically coupled to the bracelet and provided between the bracelet first and second ends, the compression element defining a compression surface compressible against the patient for substantially hemostatically sealing the percutaneous puncture; the bracelet including an attachment, the attachment including an attachment first element and an attachment second element provided respectively substantially adjacent the bracelet first and second ends; the bracelet being configurable between an open configuration in which the attachment first and second elements are disjoint from each other and a closed configuration in which the attachment first and second elements are mechanically coupled to each other and the bracelet forms a loop with the compression surface facing inwardly. With the bracelet in the closed configuration, the attachment is configurable between a locked configuration and an unlocked configuration, wherein, in the locked configuration, the attachment first and second elements are fixed with respect to each other, and in the unlocked configuration, the attachment first and second elements are movable with respect to each other such that tightening and loosening of the loop are allowed. The bracelet further comprises a safety catch configurable between a disengaged configuration and an engaged configuration, wherein, with the bracelet in the closed configuration, in the disengaged configuration, the attachment is movable between the locked and unlocked configurations, and, in the engaged configuration, with the attachment in the locked configuration, the attachment is prevented from moving to the unlocked configuration.

Typically, the attachment is moved automatically between the locked and unlocked configurations when the safety catch is in the disengaged configuration and the loop is tightened, for example only when the loop is tightened.

The tongue and bracelet serrated surfaces form a ratchet-type mechanism in which, when the safety catch is in the disengaged configuration and the bracelet is in the closed configuration: the bracelet and tongue serrated surfaces are allowed to move with respect to each other in a direction leading to tightening of the loop by automatically moving the tongue between the tongue extended and retracted configurations when the loop is tightened; and the bracelet and tongue serrated surfaces are prevented from moving with respect to each other in a direction leading to loosening of the loop when the loosening of the loop is attempted.

In some embodiments of the invention, the attachment first element includes a bracelet serrated surface provided on the bracelet and the attachment second element defines an abutment surface and a tongue provided in a substantially spaced apart relationship with respect to the abutment surface. The tongue defines a tongue serrated surface facing the abutment surface, the tongue being deformable between a tongue extended configuration and a tongue retracted configuration. In the tongue retracted configuration, the bracelet is substantially freely movable with respect to the abutment surface when inserted between the abutment surface and the tongue with the bracelet and tongue serrated surfaces facing each other. In the tongue extended configuration, the bracelet and tongue serrated surfaces engage each other and are substantially fixed with respect to each other when the bracelet is inserted between the abutment surface and the tongue with the bracelet and tongue serrated surfaces facing each other. The attachment is in the locked configuration when the tongue is in the tongue extended configuration and the attachment is in the unlocked configuration when the tongue is in the tongue retracted configuration.

Typically, the attachment second element includes a collar provided substantially adjacent the bracelet second end, the collar defining an inner peripheral surface, the abutment surface being part of the inner peripheral surface, the tongue being provided at least partially inside the collar and extending substantially longitudinally thereinto.

The safety catch is removably insertable between the tongue and the collar with the tongue between the safety catch and the bracelet serrated surface, the safety catch substantially preventing deformation of the tongue into the tongue retracted configuration when inserted between the tongue and the collar with the tongue in the tongue extended configuration and the bracelet inserted between the collar and the tongue with the body and tongue serrated surfaces facing each other. The safety catch is in the disengaged configuration when removed from the collar and the safety catch is in the engaged configuration when inserted between the tongue and the collar with the tongue in the tongue extended configuration and the bracelet inserted between the collar and the tongue with the body and tongue serrated surfaces facing each other.

The safety catch includes a locking member removably insertable between the tongue and the collar. In some embodiments of the invention, the safety catch includes a flexible element extending between the bracelet and the locking member. In some embodiments of the invention, the safety catch includes a safety catch tongue extending from the locking member, the safety catch tongue being outside of the collar when the safety catch is in the engaged configuration. In some embodiments of the invention, in the engaged configuration, the locking member is frictionally engaging the inner peripheral surface.

Typically, the tongue protrudes from the collar and defines a tongue handle provided outside of the collar, the tongue handle being graspable to move the tongue between the tongue extended and retracted configurations.

Advantageously, the proposed styptic device is relatively efficient at stopping blood flow through the percutaneous puncture while being substantially comfortable to the patient to which the styptic device is attached.

The styptic device is relatively easily manufacturable using known components and methods and is also relatively easily usable using a sequence of quick and ergonomic steps.

Advantageously, the proposed safety catch allows use of a relatively simple and easy to operate attachment, with its tongue, while securing safely the styptic device with a predetermined tension therein when required.

In another broad aspect, the invention provides a lockable flexible element, the lockable flexible element comprising: a substantially elongated and flexible body defining a body first end and a substantially opposed body second end, the body defining a body serrated surface substantially longitudinally spaced apart from the body second end; and an attachment, the attachment including a collar provided substantially adjacent the body second end; a tongue provided at least partially inside the collar and extending substantially longitudinally thereinto, the tongue defining a tongue serrated surface, the tongue being deformable between a tongue extended configuration and a tongue retracted configuration, wherein, in the tongue retracted configuration, the body is substantially freely movable through the collar when part thereof is inserted between the collar and the tongue with the body and tongue serrated surfaces facing each other, and, in the tongue extended configuration, the body and tongue serrated surfaces engage each other and are substantially fixed with respect to each other when part of the body is inserted between the collar and the tongue with the body and tongue serrated surfaces facing each other; and a safety catch removably insertable between the tongue and the collar with the tongue between the body serrated surface and the safety catch, the safety catch substantially preventing deformation of the tongue into the tongue retracted configuration when inserted between the tongue and the collar with the tongue in the tongue extended configuration and part of is the body inserted between the collar and the tongue with the body and tongue serrated surfaces facing each other.

Typically, the lockable flexible element forms a loop when the body is inserted between the collar and the tongue and the body and tongue serrated surfaces are movable with respect to each other in a direction leading to tightening of the loop by automatically moving the tongue between the tongue extended and retracted configurations when the loop is tightened and the safety catch is disengaged.

For example, the safety catch includes a locking member removably insertable between the tongue and the collar and, in some embodiments of the invention, in the engaged configuration, the locking member is frictionally engaging an inner peripheral surface of the collar. In some embodiments of the invention, the safety catch includes a safety catch tongue extending from the locking member, the safety catch tongue being outside of the collar when the safety catch is in the engaged configuration. In some embodiments of the invention, the locking member is attached to the remainder of the lockable flexible element.

Typically, but not exclusively, the body serrated surface is provided substantially adjacent the body first end. Also, typically, the tongue protrudes from the collar and defines a tongue handle provided outside of the collar, the tongue handle being graspable to move the tongue between the tongue extended and retracted configurations.

In some embodiments of the invention, the lockable flexible element is a styptic device for substantially hemostatically sealing a percutaneous puncture in a blood vessel of a patient, the lockable flexible element comprising a compression element mechanically coupled to the body and provided between the body first and second ends, the compression element defining a compression surface compressible against the patient for substantially hemostatically sealing the percutaneous puncture.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the drawings:

FIG. 2, in a top plan view, illustrates the styptic device shown in FIG. 1;

FIG. 3, in a side elevation view, illustrates the styptic device shown in FIGS. 1 and 2;

FIG. 4, in a front elevation view, illustrates the styptic device shown in FIGS. 1 to 3;

FIG. 5, in a side elevation view, illustrates the styptic device shown in FIGS. 1 to 4 with the auxiliary compression element detached therefrom;

FIG. 6, in a top plan view, illustrates the styptic device shown in FIGS. 1 to 5 with the auxiliary compression element detached therefrom;

DETAILED DESCRIPTION

Figure 1:
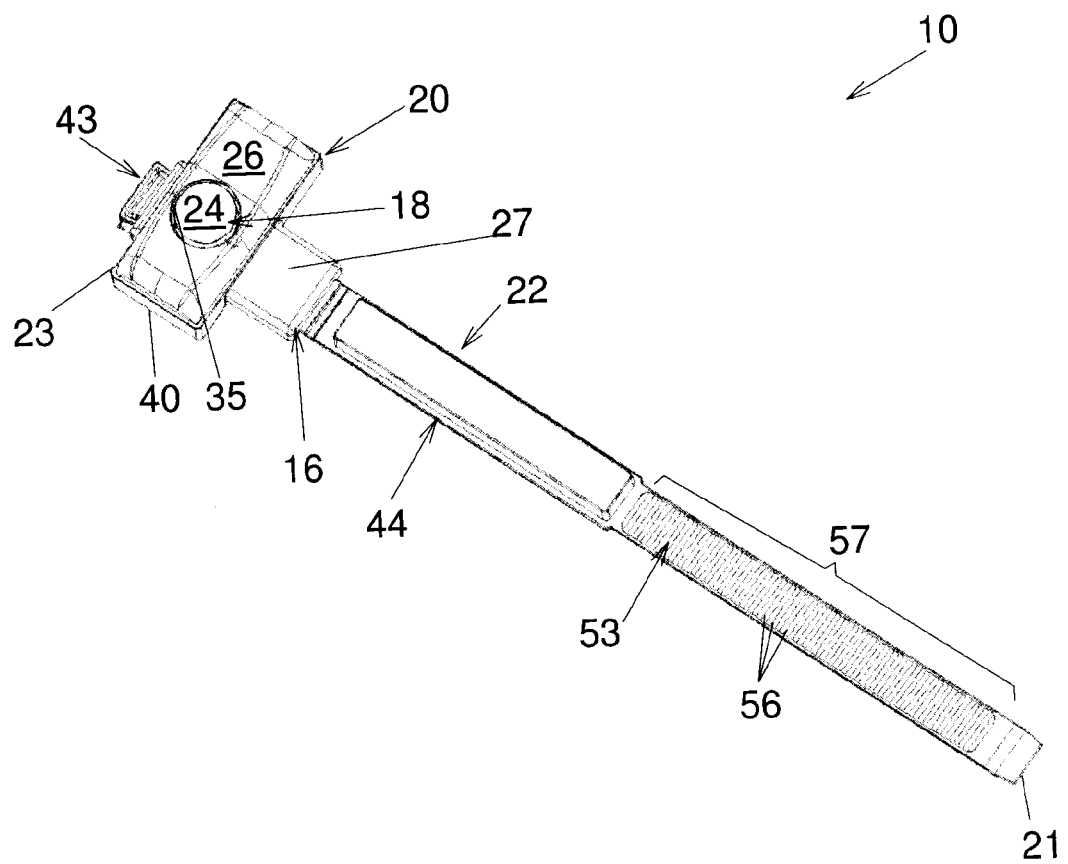
FIG. 1, in a perspective view, illustrates a styptic device in accordance with an embodiment of the present invention, the styptic device being shown with an auxiliary compression element attached.
Figure 9:
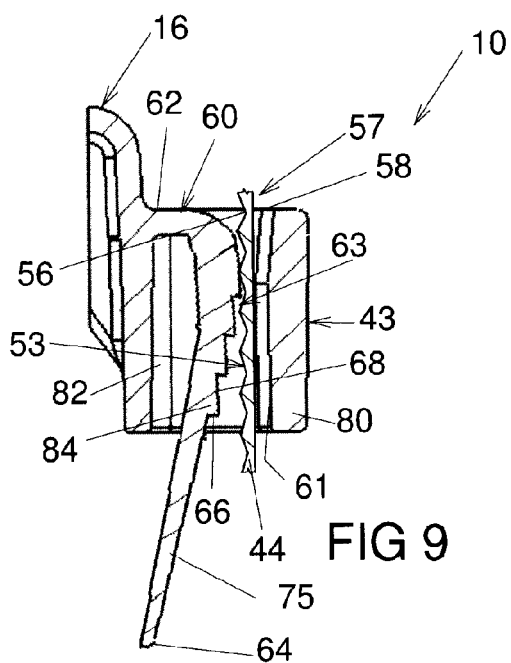
FIG. 9, in a partial side cross-sectional view taken along the line VII-VII of FIG. 6, the styptic device being shown in the open configuration with the tongue in a retracted configuration.

Referring to FIG. 1, there is shown a styptic device 10 in accordance with an embodiment of the present invention. As illustrated schematically in FIG. 11, the styptic device 10 is usable for substantially hemostatically sealing a percutaneous puncture 12 in a blood vessel 14 of a patient 11, only part of which is seen in FIG. 9. Returning to FIG. 1, the styptic device 10 includes a base 16 and a main compression element 18 extending from the base 16. An auxiliary compression element 20 is removably attachable the base 16. In some embodiments of the invention, the styptic device 10 includes a bracelet 22 mechanically coupled to the main compression element 18 for attaching the styptic device 10 to the patient 11. The bracelet 22 is configurable between an attached configuration in which the styptic device 10 is attached to the patient 11 and a detached configuration, in which the styptic device 10 is removable from the patient 11.

The bracelet defines a bracelet first end 21 and a substantially opposed bracelet second end 23. The main compression element 18 is therefore mechanically coupled to the bracelet 22 and provided between the bracelet first and second ends 21 and 23.

The main compression element 18 defines a main compression surface 24 compressible against the patient 11. The auxiliary compression element 20 defines an auxiliary compression surface 26 also compressible against the patient 11. When compressed against the patient 11 substantially in register with the percutaneous puncture 12, the styptic device 10 exerts a first pressure distribution profile on the patient 11 substantially adjacent to the percutaneous puncture 12 when the auxiliary compression element 20 is attached to the base 16 and the styptic device 10 exerts a second pressure distribution profile on the patient 11 substantially adjacent to the percutaneous puncture 12 when the auxiliary compression element 20 is detached from the base 16, the first and second pressure distribution profiles being different from each other. Such pressure distribution profiles are described in further details hereinbelow.

Advantageously, the proposed auxiliary compression element 20 varies the dimensions of and the pressure profile exerted by the styptic device 10, which increases greatly its flexibility in use on patients 11 of different morphology and in use of the styptic device 10 for hemostatically sealing percutaneous punctures 12 at different anatomical location on patients 11.

As seen in FIGS. 5 and 6, the base 16 includes a substantially parallelipiped shaped base main section 27 from which a substantially cylindrical main compression element support 28 protrudes. A substantially annular flange 30 extends substantially outwardly from the main compression element support 28 substantially away from the base main section 27 and defines a recess 32 for receiving, at least in part, the main compression element 18 therein.

The main compression element 18 is typically substantially resiliently deformable, and is made for example, of an hydrogenated copolymer of styrene, isoprene and butadiene. However, any other suitable materials are within the scope of the invention. I has been found that using a material having a Shore hardness of from about 15 A to about 50 A according to ASTM test D-2240 provided optimal results for the deformation properties of the main compression element. In a specific embodiment of the invention, the main compression element has a Shore hardness of about 30 A.

Typically, the main compression element 18 is substantially less rigid than the base 16. In some embodiments of the invention, the main compression element 18 has a shape, dimensions, and mechanical properties such that the main compression element 18 protrudes in the percutaneous puncture 12 when the main compression surface 24 is compressed against the patient 11 in register with the percutaneous puncture 12. This property is described in further details hereinbelow.

As seen in FIG. 5, in embodiments of the invention in which the main compression element 18 is received partially in the recess 32, the main compression element 18 defines a restrained portion 34 located in the recess 32 and an unrestrained portion 36 protruding from the recess 32. The restrained portion 34 is substantially prevented from deforming laterally in recess 32. The unrestrained portion 36 is substantially freely deformable to allow its partial insertion in the percutaneous puncture 12. By being substantially snuggly received in the recess 32, the restrained portion 34 helps in concentrating the deformations of the main compression element 18 in response to compressive forces substantially adjacent to the main compression surface 24, and therefore helps in the deformation of the main compression surface 24 into the percutaneous puncture 12.

The main compression element 18 is typically positioned such that the main compression surface 24 is located substantially opposed to the base 16 so that compressive forces can be easily exerted by the base 16 on the main compression element 18. To provide a substantially isotropic pressure on the percutaneous puncture 12, the main compression element 18 is typically substantially cylindrical. However, other shapes are within the scope of the present invention. Also, to facilitate positioning of the main compression element 18 relatively to the percutaneous puncture 12, the main compression element 18 is typically substantially transparent.

As seen for example in FIG. 1, the auxiliary compression element 20 is generally parallelepiped shaped and extends generally perpendicularly to the base main section 27. The auxiliary compression element 20 is provided with a substantially resiliently deformable material defining the auxiliary compression surface 26, which is typically made of a material similar to the material with which the main compression element 18 is manufactured.

In some embodiments of the invention, as shown in FIG. 1, the auxiliary compression element 20 defines an auxiliary compression element aperture 38 extending therethrough for receiving the main compression element 18 thereinto when the auxiliary compression element 20 is attached to the base 16. In these embodiments, both the main compression element 18 and the auxiliary compression element 20 contact the patient 11 when the styptic device 10 is in use. However, in alternative embodiments of the invention, no auxiliary compression element aperture 38 is provided and the auxiliary compression element 20 encloses the main compression element 18 when attached to the base 16.

As seen for example in FIG. 2, the auxiliary compression element 20 is typically substantially elongated and defines a longitudinal midpoint 90. The auxiliary compression element aperture 38 is substantially longitudinally offset from the longitudinal midpoint 90. Typically, the auxiliary compression element 20 is attachable to the base 16 in a first orientation and in a second orientation, the longitudinal midpoint 90 being laterally located with respect to the base 16 on opposite sides of the base 16 when the auxiliary compression element 20 is attached to the base 16 in the first and second orientations. In the embodiment of the invention shown in the drawings, this is achieved by having a base 16 that presents a lateral and longitudinal symmetry about the main compression element 18. In these embodiments, attaching the auxiliary compression element 20 in the first and second positions allows for using the styptic device 10 in different orientations, for example for use on the left and right wrists of the patient 11.

The auxiliary compression surface 26 is also substantially elongated. By its shape, the auxiliary compression surface 26 creates an elongated pressure profile on the patient 11, which differs from a relatively symmetrical, or disc-shaped profile crated by the main compression surface 24. The auxiliary compression surface 26 defines a central section 92 and substantially longitudinally opposed end sections 94 and 96 extending from the central section 92. The end sections 94 and 96 taper in a direction leading substantially longitudinally away from the central section 92. This shape increases the pressure exerted by the auxiliary compression surface 26 on the patient 11 as a distance from the central section 92, which is typically substantially adjacent to the percutaneous puncture 12, increases. Since many blood vessels 14, such as the radial artery, are punctured at locations that are proximal most to the skin surface of the patient 11, this configuration automatically provides a substantially uniform pressure on shallower and deeper sections of the blood vessel 14. This configuration helps in minimizing undesirable side effects of percutaneous punctures 12, such as those caused by hematomas.

The auxiliary compression element 20, when used, increases the surface area of the styptic device 10 that compresses the blood vessel 14, which improves the hemostatic properties of the styptic device 10 in relatively large patients 11. However, having the option of not using the auxiliary compression element 20 is useful in relatively small of thin patients 11.

The auxiliary compression element 20 is typically hollow and defines a main compression element peripheral wall 40 extending substantially perpendicularly from the auxiliary compression surface 26. As better seen in FIG. 4, the main compression element peripheral wall 40 defines cut out portions 42 having a profile substantially similar to the transversal cross-section of the base main section 27 at the location at which the main compression element peripheral wall 40 engages the base main section 27.

Typically, the cut out portions 42 and the auxiliary compression element aperture 38 are dimensioned so that the auxiliary compression element 20 and the base 16 are attachable to each other in a press fit relationship relatively to each other. This specific method of attachment provides for relatively easy attachment and detachment of the base 16 and auxiliary compression element 20 to and from each other. However, other methods of attachment are also within the scope of the present invention.

The main and auxiliary compression surfaces 24 and 26 are typically substantially coplanar substantially adjacent to the main compression surface 24. Therefore, when the auxiliary compression element 20 is attached to the base 16, the main and auxiliary compression elements 16 and 20 define a compression surface that is substantially smooth and without discontinuity, as seen for example in FIG. 4.

In some embodiments of the invention, the auxiliary compression element 20 defines an auxiliary compression surface 26 that is substantially concave and which defines a nadir 47 substantially adjacent to the auxiliary compression element aperture 38 and a substantially spaced apart apex 45. This configuration is advantageous to produce pressure distribution profiles on the patient 11 that are non-uniform, as described in further details hereinbelow. However, in alternative embodiments of the invention, the auxiliary compression surface 26 is of any other suitable shape, such as a substantially flat shape, or a substantially convex shape, among other possibilities. It should be noted that in the drawings, the nadir 47 is relatively shallow as the curvature of the auxiliary compression surface 26 adjacent the nadir 47 is relatively small, but other curvatures are within the scope of the invention. Also, in some embodiments of the invention, the nadir 47 is not well-defined as the auxiliary compression surface 26 is substantially flat along a portion thereof.

Referring for example to FIG. 3, the bracelet 22 includes the base 16 and a substantially elongated strap 44 extending from the base main section 27. The strap 44 is typically made out of a substantially resilient polymer, but other materials are within the scope of the invention. The strap 44 defines a strap first side 46 and an opposed strap second side 48, the strap first side being provided on the same side of the styptic device 10 as the main compression element 18. Also, the strap 44 defines a strap first end 50 and a substantially longitudinally opposed strap second end 52. The strap 44 extends from the base main section 27 at the strap first end 50 and the strap second end 52 is a free end and corresponds to the bracelet first end 21. The base main section 27 and the strap 44 are attached to each other, integrally molded together or mechanically secured to each other in any other suitable manner.

Typically, a cushion 54 is affixed onto the strap first side 46 at a location intermediate the strap first and second ends 50 and 52. The cushion 54 extends from a location substantially adjacent the base main section 27 toward the strap second end 52. The cushion 54 is typically made out of a relatively soft material, such as a gel. The cushion 54 helps in improving the comfort of the styptic device 10.

As seen in FIG. 2 for example, the bracelet includes an attachment, the attachment including an attachment first element 57 and an attachment second element 43 provided respectively substantially adjacent the bracelet first and second ends 21 and 23.

Figure 8:
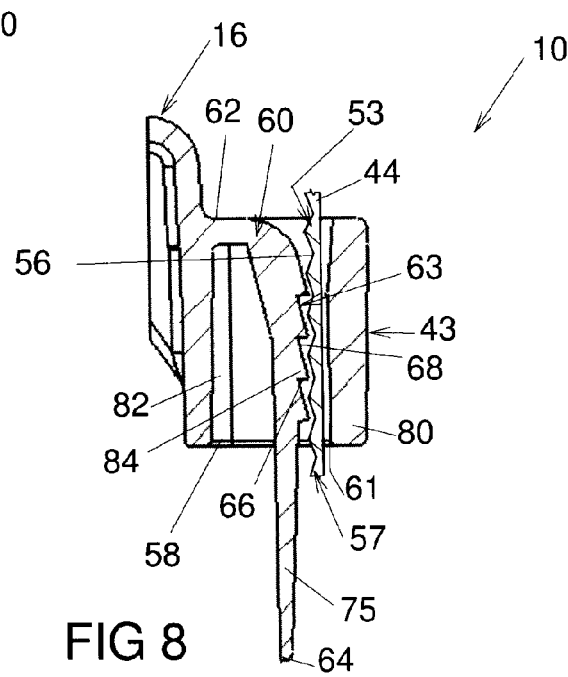
FIG. 8, in a partial side cross-sectional view taken along the line VII-VII of FIG. 6, the styptic device being shown in a closed configuration with the tongue in the extended configuration.

The bracelet 22 is configurable between an open configuration in which the attachment first and second elements 57 and 43 are disjoint from each other, as seen for example in FIG. 1, and a closed configuration in which the attachment first and second elements 57 and 43 are mechanically coupled to each other and the bracelet 22 forms a loop with the main compression surface 24 facing inwardly, the closed configuration being partially illustrated in FIG. 8. As indicated by the indication "substantially" used to define the location of the attachment first and second elements 57 and 43, the attachment first and second elements 57 and 43 are not necessarily at the ends of the bracelet 22 and a portion of the bracelet 22 may extend between the attachment first and second elements 57 and 43 and respectively the bracelet first and second ends 21 and 23. However, these portions are typically relatively short as they would protrude from the bracelet 22 in the closed configuration.

With the bracelet 22 in the closed configuration, the attachment is configurable between a locked configuration, seen in FIG. 8, and an unlocked configuration, seen in FIG. 9. In the locked configuration, the attachment first and second elements 57 and 43 are fixed with respect to each other, and in the unlocked configuration, the attachment first and second elements 57 and 43 are movable with respect to each other such that tightening and loosening of the loop are allowed. An example of specific attachment first and second elements 57 and 43 is described hereinbelow. However, any other suitable type of attachment achieving the same functionality is within the scope of the invention.

The attachment first element 57 includes a series of substantially laterally extending grooves 56 extending substantially longitudinally spaced apart from each other along a portion of the strap 44. The grooves 56 are located between the cushion 54 and the strap second end 52. The grooves 56 extend into the strap first side 46 and are used to secure the strap 44 to a limb, for example the wrist, of an intended user using the attachment second element 43. In this embodiment, the attachment first element 57 includes therefore a bracelet serrated surface 53 provided on the bracelet 22 and defined by the grooves 56.

Figure 7:
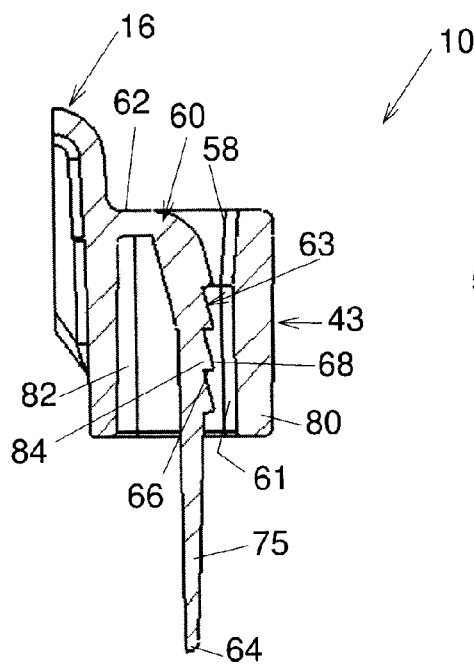
FIG. 7, in a partial side cross-sectional view taken along the line VII-VII of FIG. 6, illustrates the styptic device shown in FIGS. 1 to 6, the styptic device being shown in an open configuration with a tongue thereof in an extended configuration.

Referring for example to FIG. 7, the attachment second element 43 extends from the base 16 substantially opposed to the strap 44 and includes an abutment surface 61 and a tongue 60 provided in a substantially spaced apart relationship with respect to the abutment surface 61. The tongue 60 defines a tongue serrated surface 63 facing the abutment surface 61. The tongue 60 is deformable between a tongue extended configuration, seen for example in FIG. 8, and a tongue retracted configuration, seen for example in FIG. 9. In the tongue retracted configuration, the bracelet 22 is substantially freely movable with respect to the abutment surface 61 when inserted between the abutment surface 61 and the tongue 60 with the bracelet serrated surface 53 and tongue serrated surface 63 facing each other. In the tongue extended configuration, the bracelet serrated surface 53 and the tongue serrated surface 63 engage each other and are substantially fixed with respect to each other when the bracelet 22 is inserted between the abutment surface 61 and the tongue 60 with the bracelet serrated surface and tongue serrated surface 63 facing each other. The attachment is in the locked configuration when the tongue 60 is in the tongue extended configuration and the attachment is in the unlocked configuration when the tongue 60 is in the tongue retracted configuration.

In the specific embodiment of the invention shown in the drawings, the attachment second element 53 includes a collar 80 provided substantially adjacent the bracelet second end 23. The collar 80 defines an inner peripheral surface 82, the abutment surface 61 being part of the inner peripheral surface 82. However, in alternative embodiments of the invention, the abutment surface 61 is not part of a collar 80. For example, and non-limitingly, the abutment surface 61 could be part of a structure similar to the collar 80 but that is circumferentially interrupted by a gap. The collar 80 defines an aperture 58 delimited by the inner peripheral surface 82 and extending substantially longitudinally therethrough. For example, the aperture 58 is parallel to the recess 32 so that the aperture 58 extends generally perpendicularly to the strap 44 when the strap 44 is laid flat and coplanar with the base 16.

The tongue 60 is provided at least partially inside the collar 80 and extends substantially longitudinally into the aperture 58. The tongue 60 defines a tongue first end 62 and a substantially longitudinally opposed tongue second end 64. The tongue first end 62 is secured to the base 16 so as to position the tongue 60 inside the aperture 58 substantially in the middle thereof. The tongue second end 64 is substantially freely movable such that the tongue 60 is sufficiently resiliently deformable to allow attachment of the strap 44 as described in further details hereinbelow. Typically, the tongue 60 protrudes from the collar 80 and defines a tongue handle 75 provided outside of the collar 80, substantially adjacent the tongue second end 64. The tongue handle 75 is graspable to move the tongue 60 between the tongue extended and retracted configurations.

The tongue serrated surface 63 and the bracelet serrated surface 53 form a ratchet-type mechanism in which the bracelet and tongue serrated surfaces 53 and 63 are allowed to move with respect to each other in a direction leading to tightening of the loop formed by a closed bracelet 22 by automatically moving the tongue 60 between the tongue extended and retracted configurations when the loop is tightened.

To that effect, the tongue serrated surface 63 is defined by tongue teeth 84 substantially longitudinally spaced apart from each other along the tongue 60 and provided inside the collar 80. Typically, the tongue teeth are defined by ledges 66 extending substantially perpendicularly to the tongue 60 and sloping surfaces 68 extending therebetween. The sloping surfaces 68 are angled with respect to the ledges 66 such that the tongue teeth 84 are tapered in a direction leading from the tongue second end 64 towards the tongue first end 62.

The strap 44 and the attachment second element 43 are usable together to encircle a limb of the patient 11 to apply pressure with the styptic device 10. To that effect, the strap 44 is inserted into the aperture 58 to form a loop, with the strap first side 46 pointing inwardly. Tightening of the loop is relatively easy due to the slope of the sloping surfaces 68. However, loosening of the loop is relatively difficult due to the engagement of the ledges 66 with the grooves 56. To loosen the loop, the tongue 60 has to be deformed in the tongue retracted configuration by pressing the tongue second end 64 toward the base 16, which disengages the ledges 66 and the grooves 56 from each other.

Figure 10:
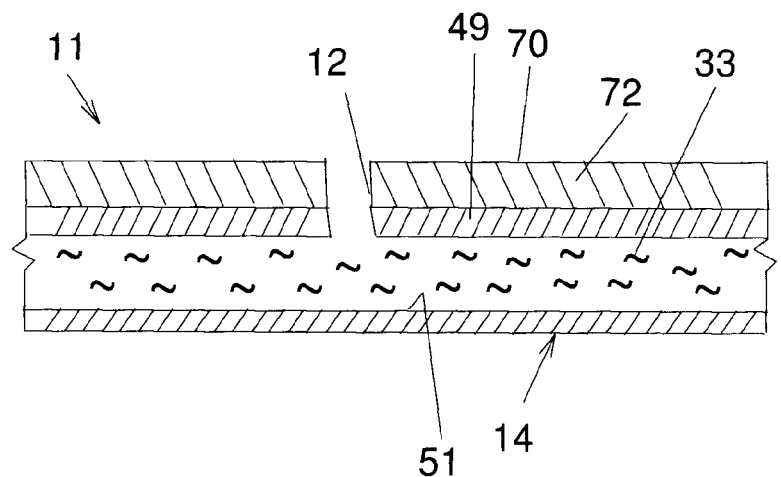
FIG. 10: in a side cross-sectional view, illustrates a percutaneous puncture.

As seen in FIG. 10, there is a need in some cases to stop blood flow from the percutaneous puncture 12. The percutaneous puncture 12 extends through an outer wall 49 of the blood vessel 14, the outer wall delimiting a lumen 51 in which blood 33 circulates. The percutaneous puncture 12 also extends through tissues extending between the skin surface 70 and the outer wall 49 to the blood vessel 14. For example, the tissue is skin tissue 72. However, in other embodiments of the invention, the blood vessel 14 is located deeper in the patient 11.

Figure 11:
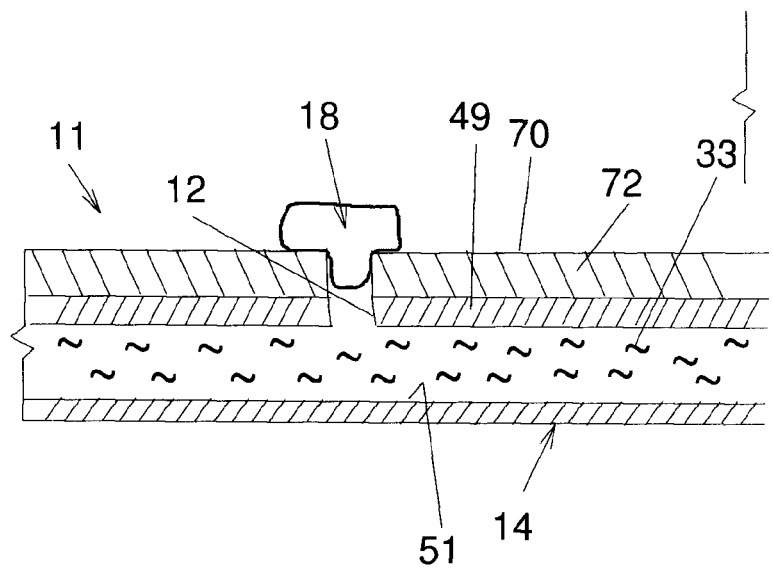
FIG. 11: in a schematic side cross-sectional view, illustrates the percutaneous puncture shown in FIG. 8 compressed with a compression element part of the styptic device shown in FIGS. 1 to 9.

FIG. 11 illustrates a method in which the compression pressure is exerted with the main compression element 18 against the patient 11 substantially in register with the percutaneous puncture 12. In this method, a compression element, in this case the main compression element 18, deforms so that the main compression element 18 protrudes in the percutaneous puncture 12. In embodiments of the invention in which the percutaneous puncture 12 defines a punctured skin portion 74 extending through skin tissues 72, it is advantageous to deform the main compression element 18 so that the main compression element 18 protrudes in the percutaneous puncture 12 such that the punctured skin portion 74 is substantially entirely filled with the main compression element 18. These embodiments allow for exerting relatively small pressures on the blood vessel 14 while preventing blood 33 from flowing out the blood vessels 14. This method is particularly advantageous as it reduces injuries to the blood vessel 14 and, therefore, facilitates healing of the patient 11. Typically, the compression pressure is decreased in steps after predetermined amounts of time until clotting has stopped bleeding completely, at which point the styptic device 10 can be removed.

In some embodiments of the invention, the auxiliary compression element 20 is used. The concave shape of the auxiliary compression element 20 creates a non-uniform pressure on the patient 11 along the auxiliary compression element 20. More specifically, when the apex 45 is positioned upstream of the percutaneous puncture 12, the pressure exerted upstream of the percutaneous puncture 12 may be larger than the compression pressure exerted at the percutaneous puncture 12. Since the upstream pressure exerted upstream of the percutaneous puncture 12 is larger than the compression pressure exerted at the percutaneous puncture 12, the blood vessel 14 may be obstructed by the upstream pressure, while allowing blood 33 from lateral vessels connected to the blood vessel 14 adjacent to the percutaneous puncture 12 to flow back towards the percutaneous puncture 12. This process conveys platelets to the percutaneous puncture 12, which helps in stopping blood flow relatively efficiently.

In alternative embodiments of the invention, the apex 45 is dimensioned so that the pressure exerted on the targeted blood vessel 14 is substantially uniform along the auxiliary compression element 20 and, as such, compensates for pressure diffusion caused by thickening of the tissue extending between the skin surface 70 and the blood vessel 14 at different locations along the blood vessel 14.

Figure 14:
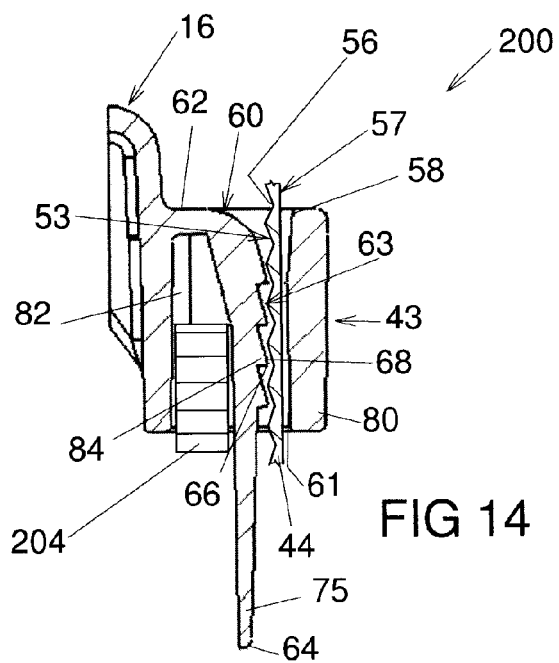
FIG. 14, in a partial side cross-sectional view taken along the line XIV-XIV of FIG. 12, illustrates the styptic device shown in FIGS. 12 and 13.
Figure 12:
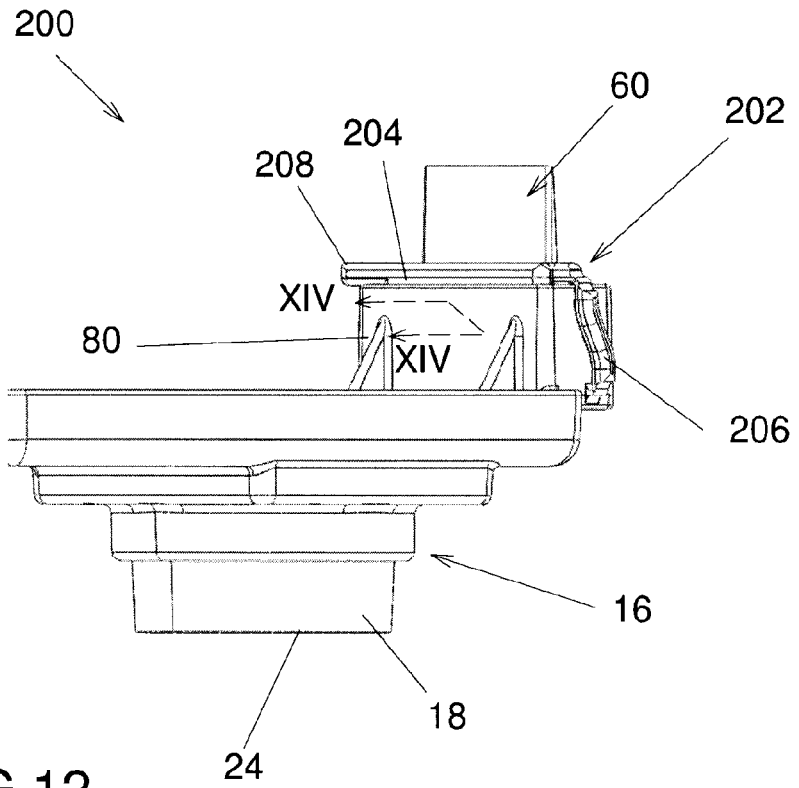
FIG. 12: in a partial perspective, illustrates a styptic device in accordance with an alternative embodiment of the present invention, the styptic device being shown with a safety catch thereof in an engaged configuration.
Figure 13:
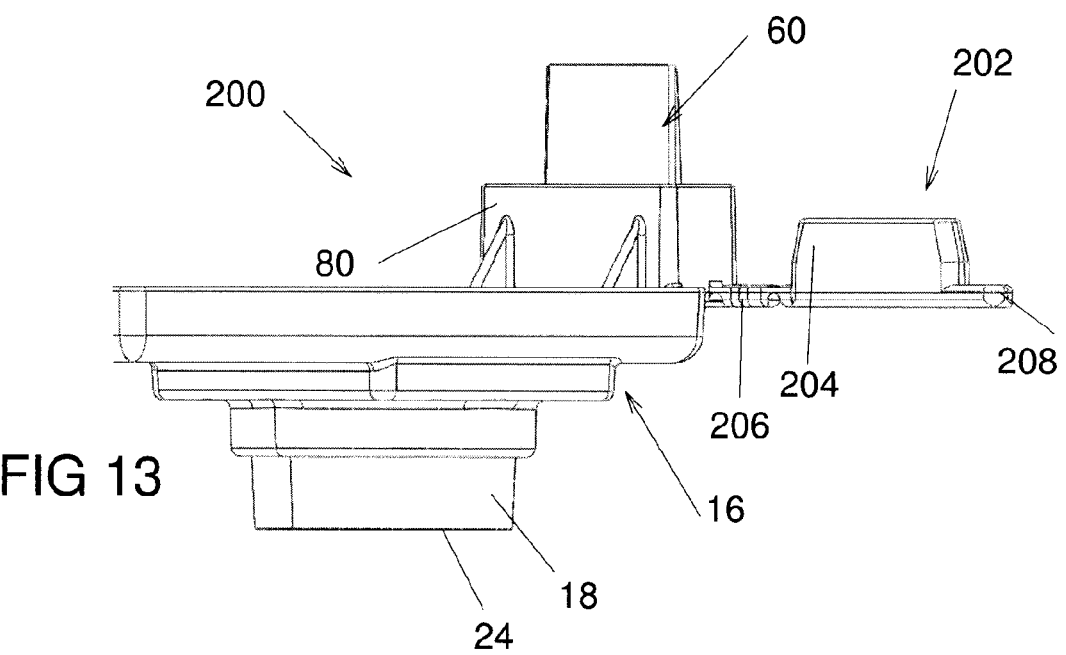
FIG. 13: in a partial perspective, illustrates the styptic device shown in FIG. 12, the styptic device being shown with a safety catch thereof in a disengaged configuration.

FIGS. 12 to 14 illustrate an alternative styptic device 200. The styptic device 200 is substantially similar to the styptic device 10 excepts that it includes a safety catch 202 for selectively locking the bracelet 22 in the attached configuration. In other words, the safety catch 202 is usable for locking the strap 44 (not shown in FIGS. 10 to 12) in position in the aperture 58.

To that effect, the safety catch 202 is configurable between a disengaged configuration, seen for example in FIG. 13, and an engaged configuration, seen for example in FIG. 12. With the bracelet 22 in the closed configuration, in the disengaged configuration, the attachment is movable between the locked and unlocked configurations, and, in the engaged configuration, with the attachment in the locked configuration, the attachment is prevented from moving to the unlocked configuration.

With the bracelet 22 forming a loop, the attachment is moved automatically between the locked and unlocked configurations when the safety catch 202 is in the disengaged configuration and the loop is tightened. In the embodiment of the invention shown in the drawings, the attachment is moved automatically between the locked and unlocked configurations with the safety catch is in the disengaged configuration only when the loop is tightened. However, in alternative embodiments of the invention, the attachment is moved automatically between the locked and unlocked configurations with the safety catch 202 is in the disengaged configuration and when the loop is loosened.

As seen in FIG. 14, the safety catch 202 is removably insertable between the tongue 60 and the collar 80 with the tongue 60 between the safety catch 202 and the bracelet serrated surface 53. The safety catch 202 substantially prevents deformation of the tongue 60 into the tongue retracted configuration when inserted between the tongue 60 and the collar 80 with the tongue 60 in the tongue extended configuration and the bracelet 22 inserted between the collar 80 and the tongue 60 with the body and tongue serrated surfaces 53 and 63 facing each other. The safety catch 202 is in the disengaged configuration when removed from the collar 80 and the safety catch 202 is in the engaged configuration when inserted in the collar 80 as described hereinabove.

Referring for example to FIG. 13, in a specific embodiment of the invention, the safety catch 202 includes a locking member 204 removably insertable between the tongue 60 and the collar 80. For example, the locking member 204 is substantially block-shaped, with a slight taper in the direction in which the locking member 204 is inserted in the collar 80. In some embodiments of the invention, the safety catch 202 is attached to the remainder of the styptic device 10. To that effect, the safety catch 202 also includes a retaining element 206 for attaching the locking member 204 to the remainder of the styptic device 200 and a safety catch tongue 208 extending from the locking member 204 for facilitating handling of the locking member 204. The safety catch tongue 208 is configured and sized for protruding from the collar 80 when the safety catch 202 is in the engaged configuration. Typically, the retaining element 206 is a flexible element extending between the bracelet 22 and the locking member 204.

The locking member 204 is configured and sized so as to be insertable in the aperture 58, as seen in FIG. 14, when the strap 44 engages the tongue 60 so as to prevent the tongue 60 from moving away from the strap 44, therefore maintaining the engagement between the ledges 66 and the grooves 56. Typically, in the engaged configuration, the locking member 204 is frictionally engaging the inner peripheral surface 82. When the locking member 204 is removed from the aperture 58, the safety catch 202 is in the disengaged configuration and the tongue 60 is free to move as describe hereinabove.

In the embodiment of the invention shown in the drawings, the locking member 204 is simply a solid piece of material of configuration and dimensions suitable for insertion in the aperture 58 between the tongue 60 and the inner peripheral surface 82. The retaining element 206 includes a deformable piece of material extending between the locking member 204 and the base 16 is configured and sized to allow movements of the locking member 204 into and out of the aperture 58. The safety catch tongue 208 protrudes from the locking member 204 and is relatively easily graspable by the fingers of an intended user.

In use, the safety catch 202 is simply inserted as described above when a desired pressure is exerted by the main compression element 18 further to suitable tightening of the strap 44 on the patient 11. To partially or completely release the pressure exerted by the main compression element 18, the safety catch 202 is removed from the aperture 58 using the safety catch tongue 208 and the tongue 60 is manipulated as described hereinabove with respect to the styptic device 10. The safety catch 202 prevents the unintended release of pressure exerted on the patient 11 by the main compression element 18. While a specific safety catch 202 has been described herein, the functionality provided by this safety catch 202 could be provided by any other suitable component.

While the safety catch 202 has been described as being usable to safely lock a styptic device 200, a similar safety catch 202 is usable with any other suitable similar device including a substantially elongated and flexible body and an attachment similar to the attachment described hereinabove that incorporates a safety catch.

Although the present invention has been described hereinabove by way of preferred embodiments thereof, it can be modified, without departing from the spirit and nature of the subject invention as defined in the appended claims.

What is claimed is:

1. A styptic device for substantially hemostatically sealing a percutaneous puncture in a blood vessel of a patient, said styptic device comprising:
    a bracelet defining a bracelet first end and a substantially opposed bracelet second end; and
    a compression element mechanically coupled to said bracelet and provided between said bracelet first and second ends, said compression element defining a compression surface compressible against said patient for substantially hemostatically sealing said percutaneous puncture;
    said bracelet including an attachment, said attachment including an attachment first element and an attachment second element provided respectively substantially adjacent said bracelet first and second ends;
    said bracelet being configurable between an open configuration in which said attachment first and second elements are disjoint from each other and a closed configuration in which said attachment first and second elements are mechanically coupled to each other and said bracelet forms a loop with said compression surface facing inwardly;
    wherein, with said bracelet in said closed configuration, said attachment is configurable between a locked configuration and an unlocked configuration, wherein, in said locked configuration, said attachment first and second elements are fixed with respect to each other, and in said unlocked configuration, said attachment first and second elements are movable with respect to each other such that tightening and loosening of said loop are allowed;
    said bracelet further comprising a safety catch configurable between a disengaged configuration and an engaged configuration, wherein, with said bracelet in said closed configuration, in said disengaged configuration, said attachment is movable between said locked and unlocked configurations, and, in said engaged configuration, with said attachment in said locked configuration, said attachment is prevented from moving to said unlocked configuration.

2. The styptic device as defined in claim 1, wherein said attachment is moved automatically between said locked and unlocked configurations when said safety catch is in said disengaged configuration and said loop is tightened.

3. The styptic device as defined in claim 2, wherein said attachment is moved automatically between said locked and unlocked configurations with said safety catch is in said disengaged configuration only when said loop is tightened.

4. The styptic device as defined in claim 3, wherein
    said attachment first element includes a bracelet serrated surface provided on said bracelet;
    said attachment second element defines an abutment surface and a tongue provided in a substantially spaced apart relationship with respect to said abutment surface, said tongue defining a tongue serrated surface facing said abutment surface, said tongue being deformable between a tongue extended configuration and a tongue retracted configuration, wherein, in said tongue retracted configuration, said bracelet is substantially freely movable with respect to said abutment surface when inserted between said abutment surface and said tongue with said bracelet and tongue serrated surfaces facing each other, and, in said tongue extended configuration, said bracelet and tongue serrated surfaces engage each other and are substantially fixed with respect to each other when said bracelet is inserted between said abutment surface and said tongue with said bracelet and tongue serrated surfaces facing each other, said attachment being in said locked configuration when said tongue is in said tongue extended configuration and said attachment being in said unlocked configuration when said tongue is in said tongue retracted configuration.

5. The styptic device as defined in claim 4, wherein said attachment second element includes a collar provided substantially adjacent said bracelet second end, said collar defining an inner peripheral surface, said abutment surface being part of said inner peripheral surface, said tongue being provided at least partially inside said collar and extending substantially longitudinally thereinto.

6. The styptic device as defined in claim 5, wherein said safety catch is removably insertable between said tongue and said collar with said tongue between said safety catch and said bracelet serrated surface, said safety catch substantially preventing deformation of said tongue into said tongue retracted configuration when inserted between said tongue and said collar with said tongue in said tongue extended configuration and said bracelet inserted between said collar and said tongue with said body and tongue serrated surfaces facing each other, said safety catch being in said disengaged configuration when removed from said collar and said safety catch being in said engaged configuration when inserted between said tongue and said collar with said tongue in said tongue extended configuration and said bracelet inserted between said collar and said tongue with said body and tongue serrated surfaces facing each other.

7. The styptic device as defined in claim 6, wherein said safety catch includes a locking member removably insertable between said tongue and said collar.

8. The styptic device as defined in claim 7, wherein said safety catch includes a flexible element extending between said bracelet and said locking member.

9. The styptic device as defined in claim 7, wherein said safety catch includes a safety catch tongue extending from said locking member, said safety catch tongue being outside of said collar when said safety catch is in said engaged configuration.

10. The styptic device as defined in claim 7, wherein in said engaged configuration, said locking member is frictionally engaging said inner peripheral surface.

11. The styptic device as defined in claim 5, wherein said tongue protrudes from said collar and defines a tongue handle provided outside of said collar, said tongue handle being graspable to move said tongue between said tongue extended and retracted configurations.

12. The styptic device as defined in claim 4, wherein said tongue and bracelet serrated surfaces form a ratchet-type mechanism in which, when said safety catch is in said disengaged configuration and said bracelet is in said closed configuration:

said bracelet and tongue serrated surfaces are allowed to move with respect to each other in a direction leading to tightening of said loop by automatically moving said tongue between said tongue extended and retracted configurations when said loop is tightened; and said bracelet and tongue serrated surfaces are prevented from moving with respect to each other in a direction leading to loosening of said loop when said loosening of said loop is attempted.

13. A lockable flexible element, said lockable flexible element comprising:

a substantially elongated and flexible body defining a body first end and a substantially opposed body second end, said body defining a body serrated surface substantially longitudinally spaced apart from said body second end; and an attachment, said attachment including:
a collar provided substantially adjacent said body second end;
a tongue provided at least partially inside said collar and extending substantially longitudinally thereinto, said tongue defining a tongue serrated surface, said tongue being deformable between a tongue extended configuration and a tongue retracted configuration, wherein, in said tongue retracted configuration, said body is substantially freely movable through said collar when part thereof is inserted between said collar and said tongue with said body and tongue serrated surfaces facing each other, and, in said tongue extended configuration, said body and tongue serrated surfaces engage each other and are substantially fixed with respect to each other when part of said body is inserted between said collar and said tongue with said body and tongue serrated surfaces facing each other; and
a safety catch removably insertable between said tongue and said collar with said tongue between said body serrated surface and said safety catch, said safety catch substantially preventing deformation of said tongue into said tongue retracted configuration when inserted between said tongue and said collar with said tongue in said tongue extended configuration and part of is said body inserted between said collar and said tongue with said body and tongue serrated surfaces facing each other.

14. The lockable flexible element as defined in claim 13, wherein said lockable flexible element forms a loop when said body is inserted between said collar and said tongue.

15. The lockable flexible element as defined in claim 14, wherein said body and tongue serrated surfaces are movable with respect to each other in a direction leading to tightening of said loop by automatically moving said tongue between said tongue extended and retracted configurations when said loop is tightened and said safety catch is disengaged.

16. The lockable flexible element as defined in claim 13, wherein said safety catch includes a locking member removably insertable between said tongue and said collar.

17. The lockable flexible element as defined in claim 16, wherein in said engaged configuration, said locking member is frictionally engaging an inner peripheral surface of said collar.

18. The lockable flexible element as defined in claim 16, wherein said safety catch includes a safety catch tongue extending from said locking member, said safety catch tongue being outside of said collar when said safety catch is in said engaged configuration.

19. The lockable flexible element as defined in claim 16, wherein said locking member is attached to the remainder of said lockable flexible element.

20. The lockable flexible element as defined in claim 13, wherein said body serrated surface is provided substantially adjacent said body first end.

21. The lockable flexible element as defined in claim 13, wherein said lockable flexible element is a styptic device for substantially hemostatically sealing a percutaneous puncture in a blood vessel of a patient, said lockable flexible element comprising a compression element mechanically coupled to said body and provided between said body first and second ends, said compression element defining a compression surface compressible against said patient for substantially hemostatically sealing said percutaneous puncture.

22. The lockable flexible element as defined in claim 13, wherein said tongue protrudes from said collar and defines a tongue handle provided outside of said collar, said tongue handle being graspable to move said tongue between said tongue extended and retracted configurations.

* * * * *